United States Patent [19]

Doorenbos

[11] Patent Number: 5,065,865
[45] Date of Patent: Nov. 19, 1991

[54] PRESSURE-REGULATED BANDAGE APPLICATOR

[76] Inventor: Daryl E. Doorenbos, R.R. 2, Box 85A, Le Mars, Iowa 51031

[21] Appl. No.: 516,070

[22] Filed: Apr. 17, 1990

[51] Int. Cl.[5] .............................................. B65D 85/67
[52] U.S. Cl. ................................. 206/409; 206/440; 242/55.53; 242/75.2
[58] Field of Search ............ 206/440, 438, 408, 409, 206/53, 411, 389, 804, 812; 242/55.2, 55.53, 75, 75.2, 75.3; 221/71

[56] References Cited

U.S. PATENT DOCUMENTS

| | | | |
|---|---|---|---|
| 1,445,022 | 2/1923 | Kimball | 242/75.2 |
| 2,684,716 | 7/1954 | Mills et al. | 206/440 X |
| 3,302,781 | 2/1967 | Rudnick | 242/55.53 |
| 3,405,983 | 10/1968 | Rutz | 242/55.53 |
| 3,647,128 | 3/1972 | Shah | 242/75.2 X |
| 4,167,253 | 9/1979 | Rutz | 242/55.53 |
| 4,807,753 | 2/1989 | Goldstein | 206/440 X |
| 4,832,229 | 5/1989 | Hackmann et al. | 221/71 X |

Primary Examiner—Paul T. Sewell
Assistant Examiner—Jacob K. Ackun, Jr.

[57] ABSTRACT

A device for wrapping elastic bandages at uniform tension including a holding compartment for holding a roll of the bandage. The bandage then is entrained over a metering roll which has an adjustable tension control to make sure of uniform tension. The metering roll has a surface formed to provide positive engagement with the bandage.

6 Claims, 1 Drawing Sheet

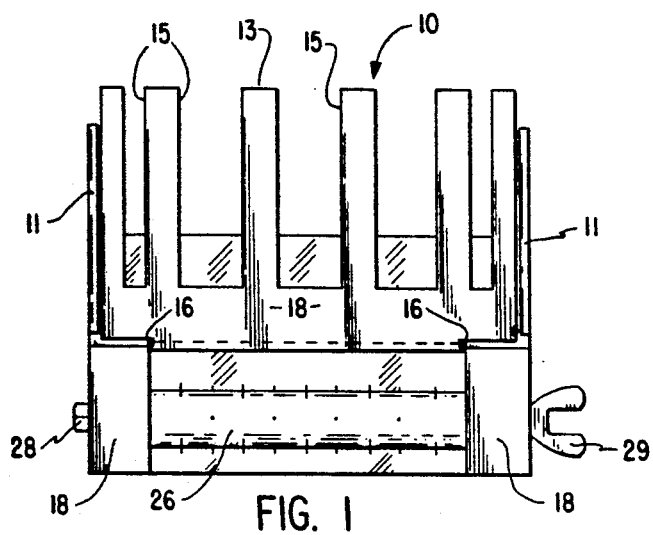
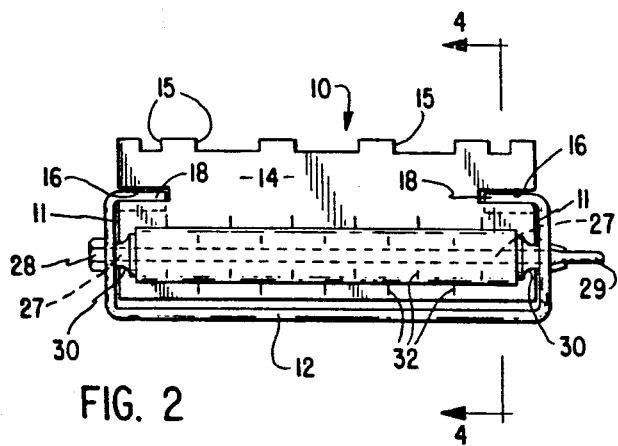
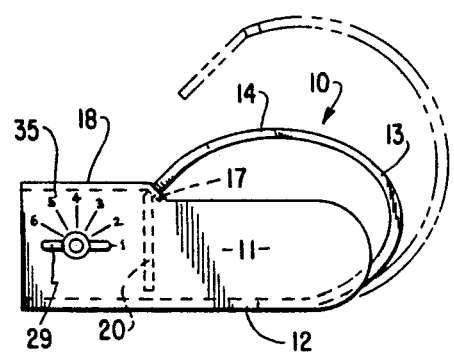
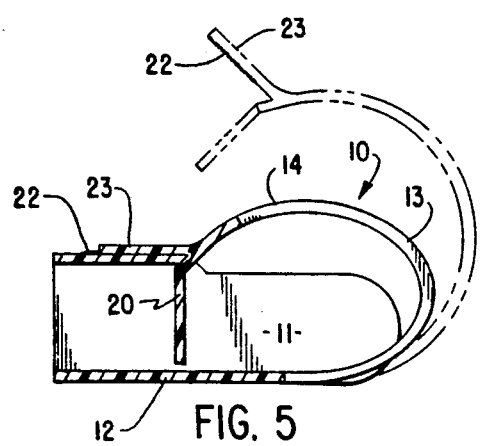
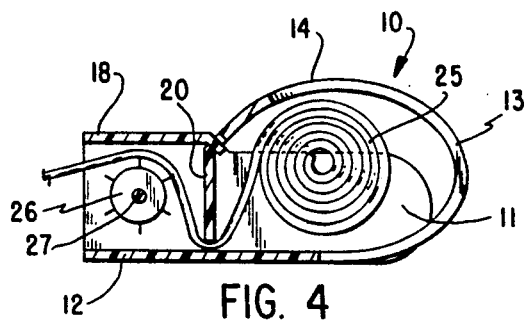

PRESSURE-REGULATED BANDAGE APPLICATOR

BACKGROUND AND SUMMARY OF THE INVENTION

This invention pertains to devices useful for holding material to be wrapped at a controlled tension, and more particularly for holding and controlling the tension on a cloth or elastic bandage as the bandage is wrapped around part of the body of a patient.

There are certain times in the treatment of surgical patients or burn patients when it is necessary to provide a regulated and near-uniform pressure on a bandage being applied. In preparation for kinds of surgery, the lower limbs of many patients are wrapped in elastic bandage under moderate tension. Presently such wrapping is usually done by skilled nurses who sense the tension required and wrap accordingly. My invention would allow such wrapping to be done by less skilled nurses, or nurses aides, allowing the skilled people to engage in more important activities in the preparation.

Burn patients also require carefully controlled pressure on bandages. This device is also useful in proving such controlled pressures even on the non-elastic bandages used for treatment of burns.

BRIEF DESCRIPTION OF THE DRAWINGS

FIG. 1 is a top plan view of the bandage holder of my invention,

FIG. 2 is a front elevational view of the holder,

FIG. 3 is an end elevational view of the holder,

FIG. 4 is a sectional view from line 4—4 of FIG. 3, and

FIG. 5 is a view similar to FIG. 4 of an alternate embodiment of the invention.

DESCRIPTION

Briefly my invention comprises a holder for a bandage and a tension roller journalled in the holder. The roller is controlled so that the force required to roll it is adjustable. The bandage is entrained over the roller and the surface of the roller is formed so that there is positive engagement of the bandage with the roller whereby the tension in the bandage is controlled.

More specifically and referring to the drawings, the holder includes an enclosure 10 formed by end walls 11 and a curved piece which forms a bottom 12, a curved back 13 and a top 14. This curved piece is somewhat flexible so that unless restrained, it will be in the open position shown by the dashed lines in FIGS. 3 and 5. In order to provide added flexibility, slots 15 are formed in the piece in the top 14 and back 13. Thus, the top 14 can be bent down and held in the closed position by any of a variety of means.

I have illustrated two possible types of latches. The first shown in FIGS. 1-4 requires side notches 16 (FIGS. 1 and 2) formed in the top. These notches are adapted to be engaged by tongues 17 formed on horizontal extension 18 of the sidewalls 11. These tongues 17 can be disengaged by pressing the top 14 downwardly so that the slots 16 slip below the tongues 17 and then the top 14 is bent back slightly so that the extension 20 will be back of the tip of the tongues 17 and can slip past to get to the open position.

The alternative shown in FIG. 5 simply uses matching strips 22 interlocking material such as "Velcro" on the extensions 18 and on a lip 23 extending toward the front from the top 14. The fastening or loosening of those strips will be obvious from the description and drawings.

The enclosure 10 serves to hold a roll 25 of bandage (FIG. 4). From the enclosure, the bandage runs under the extension 20, thence over a drum or roller 26 having an axle 27 journalled in the sidewalls 11 in front of the compartment 10. This axle 27 may take the form of a long bolt having a head 28 at one end and a thumb nut 29 threaded onto the bolt at the other. Bushings 30 on the axle 27 and between the ends of the roller 26 and sidewalls 11 hold the rollers properly spaced, and provide braking for the roller as the thumb nut 29 is tightened to press the walls 11 against the bushings 30. It will be apparent that the described device is only one possible means of controlling the tension on the bandage. I also envision using a spring mechanism or other devices.

Around the perimeter of the roller 26 there must be some means for providing a positive engagement between the roller 26 and the bandage material coming from the roll 25. I prefer to use sharpened points 32 of wire extending radially from the surface, but there may be other means. The points 32 may be considerably shorter than illustrated, but must be long enough to penetrate the bandage material enough to provide a positive engagement.

In use, the roll 25 of bandage material is placed in the compartment 10, and the end of the roll run from there over the roller 26. As the compartment 10 is closed, the extension 20 of the top will press the bandage material down as shown in FIG. 4. This provides that the material will engage the roller for nearly 90° of the circumference so that the engagement is enhanced.

The bandage material extends from the top of the roller 26 forward out of the device. It will be apparent that a lip could be provided on the bottom 12 extended which could be used to press the bandage material onto the surface being bandaged. However, this is completely unnecessary, and the bandage can simply be placed around the leg or arm or other body part, and then, without the need for any other manipulation, simply be wound onto the leg by carrying the device around it.

Tightening or loosening the thumb nut 29 will respectively increase or decrease tension on the bandage and, therefore, the pressure of the bandage on the body of the patient. In order to make possible a replication of the pressure, a scale 35 may be provided on the sidewall 11 under the nut 29. By noting the position of the nut on the scale when proper pressure is applied, and then using a similar setting of the nut, a duplicate—or near duplicate—of the pressure should be achieved.

I claim as my invention:

1. A tension controlling bandage holder comprising a housing having a compartment adapted to hold a roll of bandage material, roller means to control tension on said material when said bandage material is pulled from said housing, said roller means including a drum having sides engaging said housing and axle means supporting said axle, said axle means being adapted to rotatably journal said drum in said housing, friction control means engaged between said housing and said axle means to create friction between said housing and said drum and to adjust the friction thus created, said bandage material engaging the exterior of said drum to cause said drum to rotate whereby the adjustment of friction between the drum and the housing provides for adjustment of the tension on said bandage material as it is removed from said housing.

2. The holder of claim 1 in which said axle means includes an axle having a threaded end and the friction control means includes a nut threadably engaged with said threaded end.

3. The holder of claim 2 in which said housing includes a scale adjacent said nut, said nut including an index related to said scale whereby the position of said nut on said threaded end can be known and duplicated.

4. The holder of claim 1 in which said drum has an outer surface, sharpened points of material extending from said outer surface in position to be engaged with said bandage material whereby said bandage material is in positive engagement with said drum.

5. A tension controlling bandage holder comprising a housing having a compartment adapted to hold a roll of bandage material, said compartment including sidewalls, a back and a top, said back and top being formed of springable material, said top being in a normally open position but being moveable to a closed position, and means releasably engagable between said top and said sidewalls to hold said top in its closed position, said back and top being formed with slots to reduce the force required to move said top from its open to closed position and to provide openings through which said roll of bandage material may be observed, said housing including means to control tension on the bandage material when said bandage material is pulled from said compartment.

6. The holder of claim 5 in which said top includes an extension adapted to guide said bandage material over said drum whereby the engagement between said drum and said bandage material is enhanced.

* * * * *